United States Patent [19]

Voronkov et al.

[11] 4,215,106

[45] Jul. 29, 1980

[54] LOCAL HEMOSTATIC

[76] Inventors: Mikhail G. Voronkov, ulitsa Lermontova, 315, kv. 32; Ada T. Platonova, ulitsa Lermontova, 313, kv. 31; Vladislava Z. Annenkova, ulitsa Maratova, 29, kv. 16; Galina M. Kononchuk, ulitsa Yakobi, 26, kv. 1; Valentina B. Kazimirovskaya, ulitsa Lermontova, 289, kv. 56; Galina S. Ugrjumova, ulitsa Lermontova, 303, kv. 48; Valentina M. Annenkova, ulitsa Lermontova, 289, kv. 43, all of, Irkutsk, U.S.S.R.

[21] Appl. No.: 894,248

[22] Filed: Apr. 7, 1978

[51] Int. Cl.$^2$ .................. A61K 31/78; A61K 31/295
[52] U.S. Cl. .................. 424/81; 424/295; 526/93; 526/241
[58] Field of Search .................. 424/78, 81, 175, 295; 526/16, 241

[56] References Cited

U.S. PATENT DOCUMENTS

| | | | |
|---|---|---|---|
| 3,873,588 | 3/1975 | Osawa | 526/241 |
| 4,090,013 | 5/1978 | Ganslaw | 424/81 |

FOREIGN PATENT DOCUMENTS

| | | | |
|---|---|---|---|
| 2412090 | 9/1974 | Fed. Rep. of Germany | 424/81 |
| 46-9834 | 3/1971 | Japan | 424/81 |
| 420533 | 12/1934 | United Kingdom | 526/16 |

OTHER PUBLICATIONS

Dimitrov, Chem Abs, vol. 77, 1972, Ab. No. 116243a.
Stille, The Nat. Disp., Lea Bros, Phila., 1896, pp. 721, 724, 742, 745–749.

*Primary Examiner*—Anna P. Fagelson
*Attorney, Agent, or Firm*—Haseltine, Lake & Waters

[57] ABSTRACT

A local hemostatic comprising an active principle which is the incomplete ferric salt of polyacrylic acid of the formula:

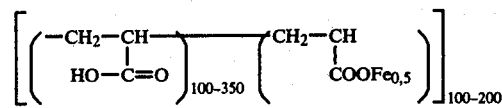

in combination with a pharmaceutical solvent which is water or physiological solution. The active principle content is 1 to 2 percent by weight.

2 Claims, No Drawings

LOCAL HEMOSTATIC

FIELD OF THE INVENTION

The present invention relates to medicine and, more particularly, to a local hemostatic.

The proposed hemostatic serves to arrest parenchymatous hemorrhage in different organs.

BACKGROUND OF THE INVENTION

The known hemostatics, such as hydrogen peroxide, alum and ferric chloride, are not effective enough, whereas the use of such a natural hemostatic as thrombin is limited because of its high cost and side effects it may produce (for example, when thrombin gets into the blood channel it may lead to intravalscular coagulation of the blood).

There are also known polymer-based synthetic hemostatics. These include complexes comprising adrenaline and the copolymer of polyvinyl furfural and maleic acid; graft copolymers of cellulose and acrylic acid; cyan-acrylate glue; and oxidized cellulose and its complexes.

The foregoing hemostatic preparations are disadvantageous in that they are hard to produce and in that they only act upon separate components of the blood coagulation system. The coagulation time of the best of these preparations is 20 to 60 seconds (the control time being 120 seconds).

SUMMARY OF THE INVENTION

It is an object of the present invention to provide a new effective local hemostatic which would coagulate blood proteins and thus produce a hemostatic effect in both normal and damaged blood coagulation systems.

The foregoing object is attained by providing a local hemostatic comprising an active principle which is the incomplete ferric salt of polyacrylic acid of the formula:

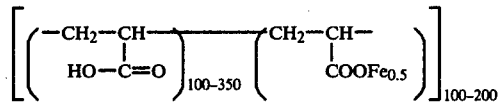

in combination with a pharmaceutical solvent which is water or physiological solution (0.85% solution of sodium chloride), the active principle content being 1 to 2 percent by weight.

DETAILED DESCRIPTION OF THE INVENTION

The interaction of the proposed hemostatic with native blood, oxalic plasma, serum and heparinized blood was studied in vitro. In all cases, it took 1 to 2 seconds to produce a firm clot of proteins.

Experiments were also carried out on mice; these were aimed to study the arrest of hemorrhage from incisions in the tail area. The preparation of this invention stopped the bleeding immediately. In another series of experiments, wounds 0.7 to 1.0 cm long were inflicted upon livers of rats; it took 5 seconds to stop the hemorrhage with the use of the proposed hemostatic. After an infiltration of a portion of the liver with a solution of the imcomplete ferric salt of polyacrylic acid, wounds subsequently inflicted in that portion of the liver produced no hemorrhage. No side effects, such as irritation or edema, nor toxic effects were observed in the experimental animals. In the case of rats, $LD_{50}=840$ mg/kg.

The proposed preparation was used to produce local hemostasis in 34 patients. Of these, there were 6 cases of hemophilia due to the extraction of teeth; 2 cases of hemophilia due to the removal of a pseudotumor and osteosynthesis of the hip; 6 cases of other pathological changes in the blood coagulation system (Werlhof's disease, hemolytic anemia, hypoplastic anemia, Marchiafava-Micheli disease); 5 cases of lung operations; 5 cases of operations on the gastroenteric tract; 1 case operated on for a thyrotoxic goiter; 5 cases of cholecystectomy; 3 cases of secondary erosive hemorrhage; and 1 case of cardiovascular insufficiency with nasal bleeding.

In all the above cases, the hemostatic of the present invention was used to stop diffuse hemorrhage from small vessels at the following stages of an operation:

(1) incision of the skin;
(2) incision of the subcutaneous fat;
(3) incision of aponeurosis;
(4) arrest of hemorrhage in the bed of a removed spleen;
(5) arrest of hemorrhage in the bed of a removed gallbladder;
(6) arrest of hemorrhage resulting from blunt dissection of commissures in the abdominal cavity;
(7) arrest of hemorrhage resulting from dissection of commissures in the pulmonary and parietal pleura;
(8) arrest of hemorrhage in parenchymatous organs (in the liver in cases of biopsy, as well as in a damaged spleen and lungs);
(9) arrest of hemorrhage during the extraction of teeth.

The proposed preparation produces a good hemostatic effect even in patients with a poor blood coagulability. It brings about hemostasis faster than any other hemorrhage arresting drug or technique, and thus considerably reduces losses of blood.

No adverse side effects are produced both during and after an operation. There are no contraindications to the use of the proposed hemostatic.

The preparation is used in two ways:

(1) gauze drains are saturated with 1- or 2-percent solution of the preparation in water or physiological solution, whereupon the drains are dried and autoclaved during 30 minutes at a temperature of 120° C. and a pressure of 1.2 atm.;
(2) gauze or cotton wool tampons are saturated with the above-mentioned solution and used without drying.

In order to arrest hemorrhage, a dry gauze drainer or a wet tampon is applied to a bleeding area, whereupon an elastic clot is produced and the hemorrhage is stopped.

The hemostatic of this invention is a yellow-brownish transparent odorless solution with a pH of 3.0 to 3.4. The proposed preparation is sterilized at 120° C. during 30 minutes. Upon sterilization, the shelf life of the preparation is not less than one year.

The preparation's active principle, i.e. the incomplete ferric salt of polyacrylic acid, is obtained by polymerizing acrylic acid in an aqueous solution in the presence of this reduction-oxidation system: $FeSO_4 \cdot (NH_4)_2SO_4 \cdot 6H_2O / K_2S_2O_8$. The polymerization is carried out at a temperature of 25° C.; $FeSO_4 \cdot (NH_4)_2SO_4 \cdot 6H_2O$ is taken in an amount of 0.8 to 2.2 percent by weight. The concentration of acrylic acid in the solution is no more than 20 percent by volume. The resulting viscous red mass is dissolved in water to a concentration of 3 to 4 percent. In order to remove the initiator and unreacted acrylic acid, the incomplete ferric salt of polyacrylic acid (the polymer) is either reprecipitated from the aqueous solution with a saturated aqueous solution of sodium chloride with a subsequent dialysis of the polymer solution aimed to remove the captured NaCl, or is passed through a strong-base anion-exchange resin. The purified polymer solution may be diluted to a concentration of 1 to 2 percent (in this form it is ready for use), or dried at a temperature of 50° C. and the atmospheric pressure. The yield of incomplete ferric salt of polyacrylic acid is 85-95 percent of the theoretical; this salt is a glasslike brittle mass of a orange-brownish color. It is readily soluble in water, but is insoluble in alcohols, dioxane, aliphatic hydrocarbons and their chlorine derivatives. The molecular weight of the preparation's active principle is $7 \cdot 10^5$ to $5 \cdot 10^6$. The iron content in the salt is 0.1 to 0.3 percent by weight.

The advantages of the proposed local hemostatic are as follows:

(1) the preparation reduces the coagulation time 4 to 12 times, as compared to the best heretofore known preparations; in animals, the coagulation time is 2 to 5 seconds with 120 seconds in control animals;

(2) the preparation effectively coagulates blood proteins, wherefore is can be used with both normal and affected blood coagulation systems;

(3) the preparation of this invention is produced from cheap and readily available raw materials; the production process is carried out in a single step which is well known in the art.

A better understanding of the present invention will be has from a consideration of the following examples which illustrate the production of the preparation's active principle, i.e. incomplete ferric salt of polyacrylic acid.

EXAMPLE 1

28.8 g (0.4 mole) of freshly distilled acrylic acid is dissolved in 120 ml of distilled water. 1.7 g of $K_2S_2O_8$ dissolved in 20 ml of water is added to the solution thus obtained. The reaction mixture is then intensively stirred, as a solution of 0.24 g of $FeSO_4.(NH_4)_2SO_4.6H_2O$ in 2 ml of water is added thereto. The transparent viscous red mass thus produced is dissolved in 1 l of water. In order to remove the unreacted acrylic acid, the incomplete ferric salt of polyacrylic acid (the polymer) is reprecipitated two or three times from an aqueous solution, using a saturated aqueous solution of sodium chloride. The polymer is then again dissolved in water and dialyzed to remove the captured NaCl. The purified solution is dried at 50° C. Instead of salting out, the solution may be passed through an anion exchanger.

The iron content in the polymer thus produced is 0.11 percent by weight.

EXAMPLE 2

28.8 (0.4) mole of freshly distilled acrylic acid is dissolved in 120 ml of distilled water; 1.7 g of $K_2S_2O_8$ dissolved in 20 ml of water is then added to the solution. The reaction mixture is intensively stirred, as a solution of 0.43 g of $FeSO_4.(NH_4)_2SO_4.6H_2O$ is added thereto. After this stage, the process is carried out as in Example 1.

The iron content in the polymer thus produced is 0.2 percent by weight.

EXAMPLE 3

The process is conducted as in Example 1, but $FeSO_4.(NH_4)_2SO_4.6H_2O$ is taken in an amount of 0.63 g. The iron content in the polymer is 0.3 percent by weight.

What is claimed is:

1. A local hemostatic composition comprising, as active ingredient, a hemostatically effective amount of a water soluble incomplete salt of a polyacrylic acid of the formula

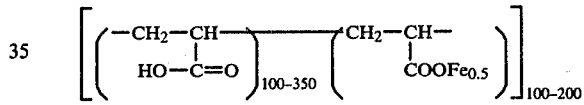

said salt prepared by polymerizing acrylic acid in the presence of an reduction-oxidation system, $FeSO_4.(NH_4)_2SO_4.6H_2O/K_2S_2O_8$, to yield a salt having an iron content of 0.1–0.3%, said active ingredient being present in an amount of from 1 to 2% by weight in a pharmaceutical carrier.

2. A method of use of a composition of claim 1 as a hemostatic agent by applying a hemostatically effective amount of said composition to a bleeding or hemorrhaging area in a patient having a bleeding or hemorrhaging area.

* * * * *